(12) United States Patent
Corrias et al.

(10) Patent No.: US 6,776,048 B2
(45) Date of Patent: Aug. 17, 2004

(54) TRIBOLOGICAL TEST APPARATUS

(75) Inventors: Silvio Corrias, Orbassano (IT); Paolo Faraldi, Sanremo (IT); Valter Stabielli, Orbassano (IT)

(73) Assignee: C.R.F. Societa Consortile Per Azioni, Orbassano (IT)

( * ) Notice: Subject to any disclaimer, the term of this patent is extended or adjusted under 35 U.S.C. 154(b) by 12 days.

(21) Appl. No.: 10/359,831

(22) Filed: Feb. 7, 2003

(65) Prior Publication Data

US 2003/0177840 A1 Sep. 25, 2003

(30) Foreign Application Priority Data

Feb. 8, 2002 (IT) ..................................... TO2002A0117

(51) Int. Cl.[7] .................................................. G01N 3/08
(52) U.S. Cl. ......................................................... 73/819
(58) Field of Search ........................ 73/818, 819, 821, 73/862.041, 862.042, 862.043

(56) References Cited

U.S. PATENT DOCUMENTS 5,679,883 A * 10/1997 Wedeven ....................... 73/10
6,186,103 B1 * 2/2001 Schafer et al. ........... 123/90.17
6,231,732 B1 * 5/2001 Hollars et al. ......... 204/298.26
6,641,322 B2 * 11/2003 Narasimhan et al. ......... 403/29

* cited by examiner

Primary Examiner—Max Noori
(74) Attorney, Agent, or Firm—Kenneth L. Sherman; Myers Dawes Andras & Sherman LLP (57) ABSTRACT

A tribological test apparatus has a supporting structure, to which are fitted a central shaft rotating about a respective axis, and three peripheral shafts rotating about respective axes equally spaced angularly about the axis of the central shaft; the central shaft and peripheral shafts respectively support a central specimen and three peripheral specimens facing one another radially; and the apparatus has three actuators, each for exerting on a relative peripheral specimen a force directed towards the central specimen, and a guide and slide device associated with each peripheral shaft to enable each peripheral specimen, in use, to translate radially towards the central specimen and exert a contact pressure on the central specimen by virtue of the force generated by the relative actuator.

27 Claims, 5 Drawing Sheets

TRIBOLOGICAL TEST APPARATUS

The present invention relates to a tribological test apparatus, and in particular to an apparatus for performing contact surface fatigue tests by subjecting the surface of disk-shaped specimens to cyclic Herzian stress, i.e. cyclic contact pressure.

BACKGROUND OF THE INVENTION

As is known, tribology studies the interaction, and in particular friction, wear, and lubrication phenomena, of surfaces of contacting bodies under load and in relative motion. In tribology, a need is particularly felt to determine the life of machine components subjected to rolling contact wear caused by cyclic mechanical stress of a surface in rolling contact with at least one other body; which stress, repeated over time, induces fatigue damage phenomena, which are manifested by the removal of fragments of material from the surface involved. Rolling contact wear is one of the main factors responsible for the failure of components such as rolling bearings, gears, and wheel-rail couplings, and is fairly difficult to detect at the initial stages, on account of initial fatigue (particularly in the case of surface hardened components) producing cracks beneath the outer contact surface.

When sufficiently widespread, the cracks emerge on the outer contact surface, and may result in splintering and, therefore, in immediate impairment in component efficiency, caused by a drastic change in component geometry.

The process defined by cyclic stress resulting in component wear and, eventually, failure as described above is known as "rolling contact fatigue", and the above surface damage as "pitting".

Pitting phenomena can be divided into two classes: initial or micropitting compatible with functioning of the component; and destructive or macropitting marked by the formation of macroscopic damage.

To determine the life of components subjected to in-service rolling contact fatigue, apparatuses are known for laboratory testing disk-shaped specimens made of the same material (both the base material and any surface treatment) as the study component: the specimens are rolled mutually, and the number of Hertzian contact load cycles to which the specimen surfaces are subjected upon the onset of macropitting phenomena in the specimens is recorded.

Such known apparatuses can be divided into two types, a first of which comprises two specimens rotated at variable, independent speeds and pushed one against the other by a variable load. The asymmetry of the system and the single contact region between the surfaces obviously limit the loads that can be applied, and greatly increase test time. For this reason, a second type of apparatus has been proposed comprising four specimens—one central and three peripheral—which are fitted in fixed positions to respective parallel shafts rotating about respective axes. The peripheral specimens are spaced 120° apart about and in contact with the central specimen, and are pushed radially and simultaneously against the central specimen as they are rotated. The peripheral specimens are fitted to and project from relatively long transmission shafts, the flexural elasticity of which enables the peripheral specimens, when subjected to radial thrust, to oscillate radially by relatively small amounts (about a tenth of a millimeter) and so exert pressure on the central specimen as they roll mutually. Three Hertzian contact load cycles are thus performed on the central specimen at each turn.

Radial thrust is applied on the peripheral specimens using pressurized oil, which also provides for lubrication and is fed into a radial gap between each peripheral specimen and a relative C-shaped body fixed adjacent to the contact surface of the peripheral specimen on the diametrically opposite side to the central specimen.

The presence of pitting phenomena is determined using an accelerometer fitted to the central specimen shaft, and the readings of which are used to calculate the power spectrum integral, i.e. energy, associated with the main frequency harmonics of the shaft. When the energy calculated exceeds a given (experimentally determined) threshold indicating the onset of pitting phenomena, testing is stopped to avoid subjecting the apparatus to dangerous vibration caused by surface damage to, and a variation in the geometry of, the specimens. Obviously, the total number of load cycles withstood by the central specimen (three times that of the peripheral specimens) is the significant value by which to compare tests and assess the specimen materials.

The above known apparatuses are unsatisfactory by employing oil, necessarily suitable for use in hydraulic systems, to apply the peripheral to central specimen contact load, and therefore cannot be operated for tribological testing using just any lubricant, and in particular the actual in-service lubricants of the mechanical parts for testing.

Moreover, known apparatuses of the above type are extremely complex, and therefore expensive, to produce and assemble. That is, the specimens and C-shaped bodies must be machined and positioned extremely accurately to ensure the relative oil gaps are all the same size and as uniform as possible during testing, and so ensure the oil flow acting directly on the peripheral specimens exerts perfectly balanced thrusts in perfectly radial directions with respect to the central specimen.

Once the geometry of the apparatus is defined, the specimens cannot normally be replaced with others of different shape and/or size, which would also mean replacing the C-shaped bodies and shaft bearings to adapt to the size and shape of the new peripheral specimens.

Moreover, when the peripheral specimens are subjected to thrust by the pressurized oil, the transmission shafts flex elastically towards the central specimen as they rotate, and so undergo combined rotation and bending fatigue stress which tends to reduce their working life.

Known apparatuses of the above type cannot normally be used to simply determine surface wear of the specimens, owing to the extremely small maximum travel of the peripheral specimens to and from the central specimen, so that, when wear exceeds the maximum travel, the peripheral specimens can no longer be brought into contact with the central specimen.

Finally, to determine the instant marking the onset of pitting phenomena, a complex, high-cost computing and control device is required to stop testing immediately pitting phenomena arise.

SUMMARY OF THE INVENTION

It is an object of the present invention to provide a tribological test apparatus designed to provide a straightforward, low-cost solution to the drawbacks of the aforementioned known apparatuses.

According to the present invention, there is provided a tribological test apparatus comprising:

a supporting structure;

a central shaft extending along a first axis, connected to said supporting structure to rotate about said first axis, and supporting a central specimen;

at least three peripheral shafts extending along respective second axes equally spaced about said first axis, connected to said supporting structure so as each to rotate about the respective second axis, and supporting respective peripheral specimens radially facing said central specimen;

push means for exerting on each said peripheral specimen a force directed towards said central specimen; and relatively mobile means associated with said peripheral shafts to enable each said peripheral specimen, in use, to move radially towards said central specimen and exert a contact-pressure on said central specimen under the action of said force;

characterized in that said push means comprise, for each said peripheral specimen, a movable push member for exerting said force along a push axis intersecting said first and said second axis;

Said relatively mobile means preferably comprise, for each said peripheral shaft, guide and slide means enabling said peripheral specimen to translate between a radial contact position radially contacting said central specimen, and a radially detached position radially detached from said central specimen; transmission means being provided for rotating each said peripheral shaft independently of its translation.

BRIEF DESCRIPTION OF THE DRAWINGS

A non-limiting embodiment of the invention will be described by way of example with reference to the accompanying drawings, in which.

DETAILED DESCRIPTION OF THE INVENTION

Figure 1:
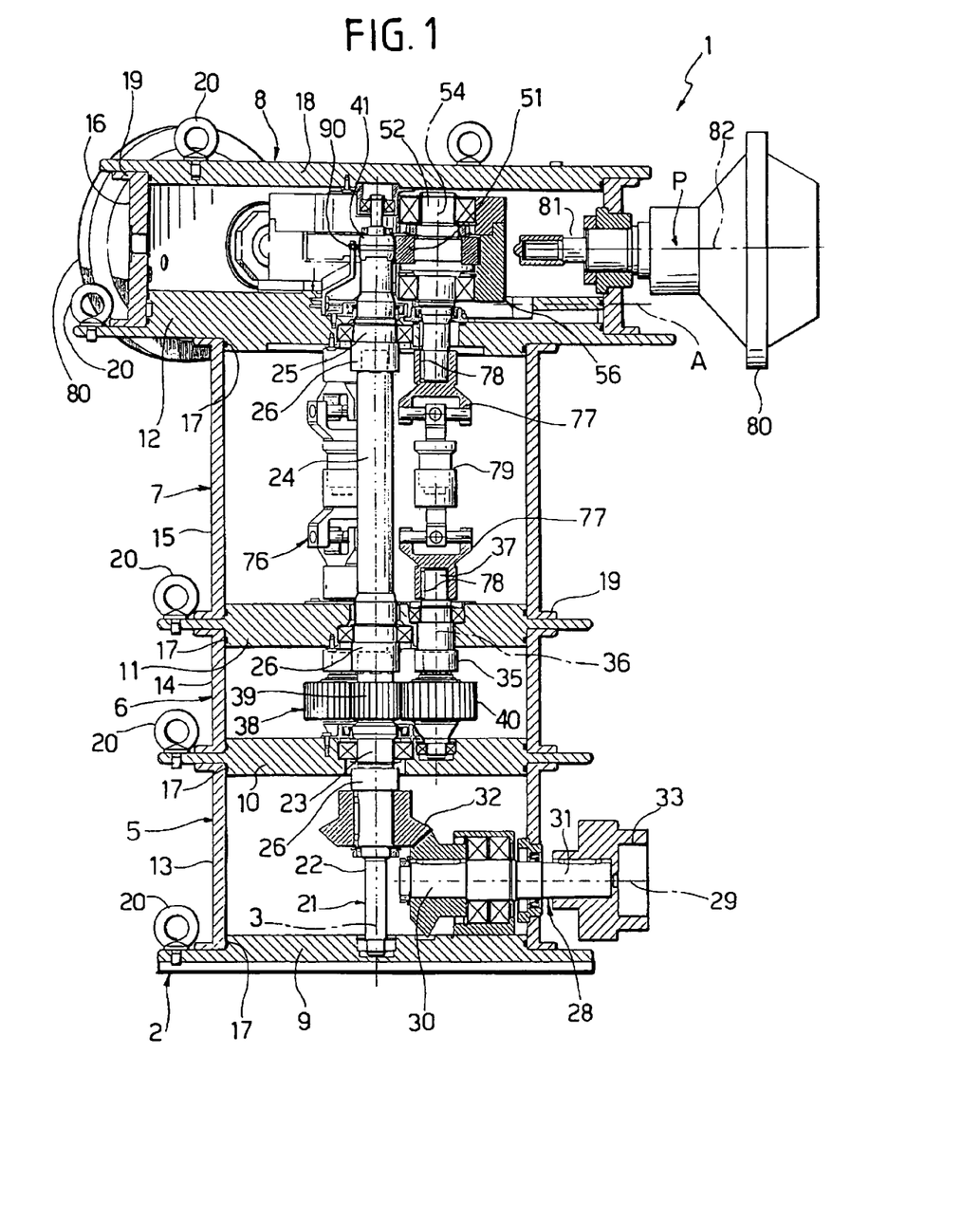
FIG. 1 shows a cross section of a preferred embodiment of the tribological test apparatus according to the present invention.

Number 1 in FIG. 1 indicates a tribological test apparatus comprising a substantially cylindrical supporting structure 2 extending vertically along a respective axis 3.

Structure 2 comprises four modules 5, 6, 7, 8 stacked axially and in turn comprising respective plates 9, 10, 11, 12 perpendicular to axis 3, and respective cylindrical boxes 13, 14, 15, 16 fitted in fluidtight manner to respective plates 9, 10, 11, 12 by sealing members 17. Plate 9 defines a base designed to rest on and fit to a test bench (not shown), and has substantially the same outside diameter as the top module 8 to impart stability to apparatus 1. Plates 10, 11, 12 axially separate respective modules 6, 7, 8 from respective modules 5, 6, 7 underneath, while module 8 is closed at the top by a lid or plate 18 fitted in fluidtight manner to box 16.

The axial ends of boxes 13, 14, 15, 16 have flanges 19 connected integrally and releasably to plates 9, 10, 11, 12, 18, preferably by means of screws and locating pins (not shown), and plates 9, 10, 11, 12, 18 have eyebolts 20 for lifting plates 9, 10, 11, 12, 18 and modules 5, 6, 7, 8.

As shown in FIG. 1, structure 2 houses a central shaft 21 extending along axis 3 and comprising four axially aligned portions 22, 23, 24, 25 connected to one another in angularly fixed, axially removable manner, e.g. by means of splined couplings 26 (not shown in detail). Portions 22, 23, 24, 25 are fitted to respective modules 5, 6, 7, 8, and are connected in fluidtight manner and in fixed positions to plates 9, 10, 11, 12, 18 to rotate about axis 3.

Shaft 21 is rotated by an input shaft 28 extending in fluidtight manner through box 13 along a horizontal axis 29 perpendicular to axis 3, and fitted in a fixed position to module 5 to rotate about axis 29.

Shaft 28 has two opposite ends 30, 31; end 30 is connected to shaft 21 by a bevel gear transmission 32; and end 31 is fitted integrally with a coupling 33 for connection to a drive motor (not shown) controlled, in use, to rotate shaft 21 at constant angular speed regardless of load.

Shaft 21 transmits rotation, in module 6, to three shafts 35 (only two shown in FIG. 1), which extend along respective axes 36 parallel to and equally spaced angularly about axis 3. Shafts 35 are connected in fluidtight manner and in fixed positions to plates 10, 11 to rotate about axes 36, comprise respective end portions 37 projecting inside module 7, and are rotated by a gear train 38 comprising a cylindrical gear 39 fitted integrally to portion 23 of shaft 21, and three cylindrical gears 40 fitted integrally to respective shafts 35 and meshing with gear 39. Gear 39 and the three gears 40 can be variously combined to transmit rotation at various velocity ratios.

Figure 4:
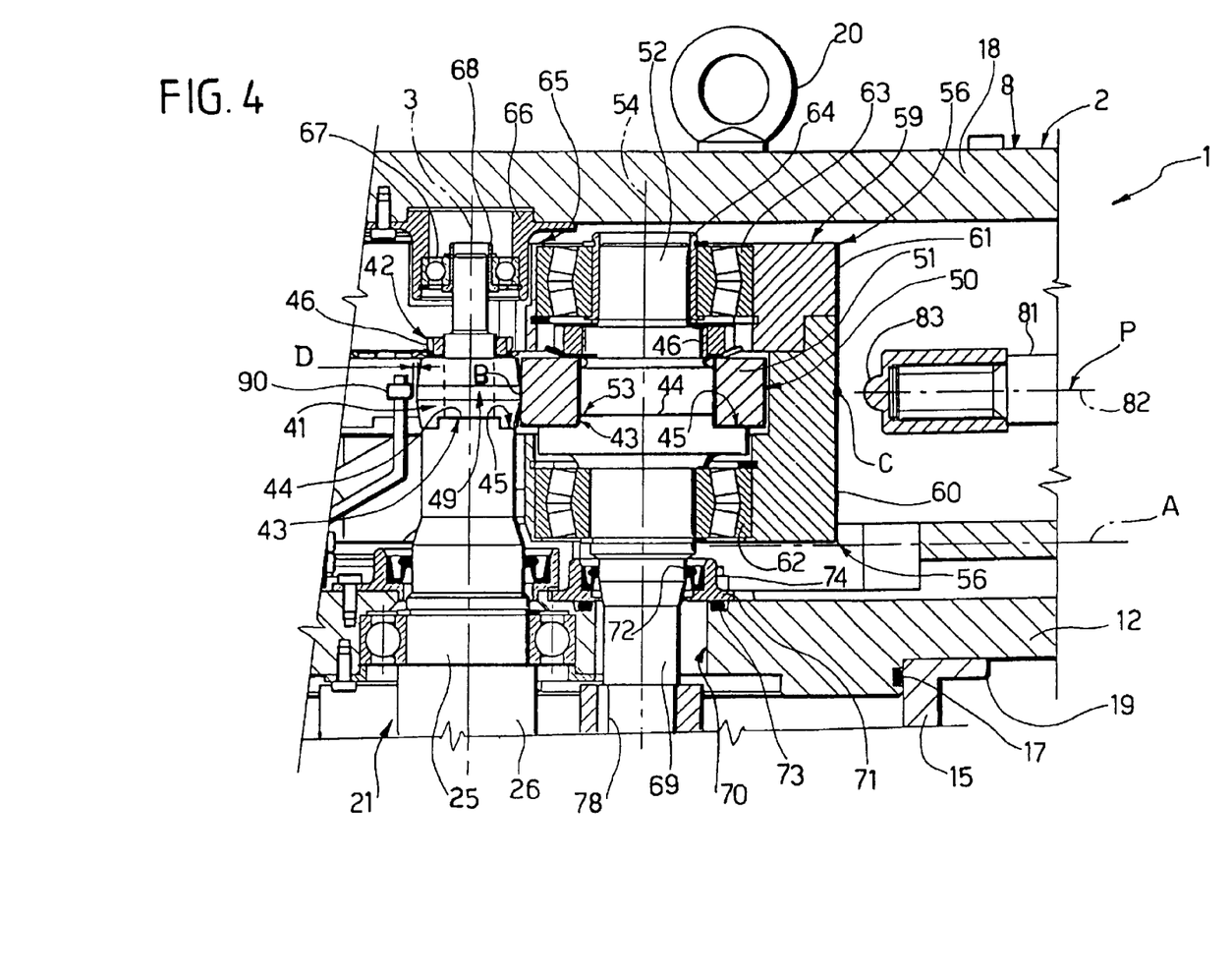
FIG. 4 is similar to and shows a larger-scale detail of FIG. 3.

With reference to FIG. 4, in module 8, portion 25 of shaft 21 rotates a central specimen 41 defined by a disk fitted coaxially to portion 25. Specimen 41 is fixed to portion 25 by a coupling device 42 comprising a groove 43 formed in specimen 41 and perpendicular to axis 3, a rib 44 extending upwards from an axial shoulder 45 of portion 25 to engage groove 43 in an angularly fixed position, and a ring nut and washer device 46 which keeps specimen 41 resting axially on shoulder 45 and engaging rib 44.

Specimen 41 has a lateral surface 49 radially contacting the lateral surfaces 50 of three peripheral specimens 51, which are disk-shaped, are all the same size, and are each fitted to a respective shaft 52 by a coupling device 53, the component parts of which are similar to and indicated using the same reference numbers as those of device 42.

Figure 2:
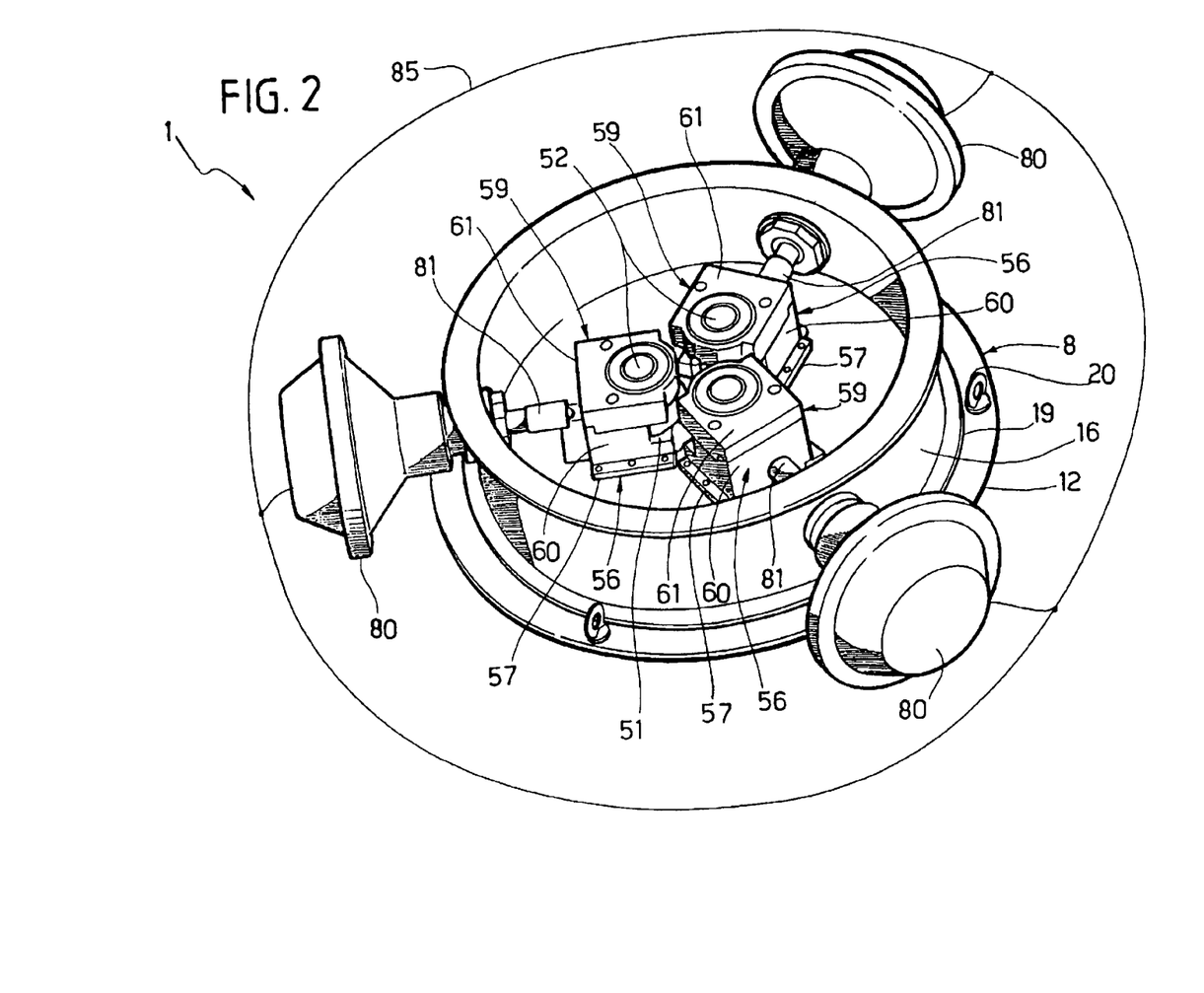
FIG. 2 shows a schematic view in perspective of a portion or module of the FIG. 1 apparatus.
Figure 3:
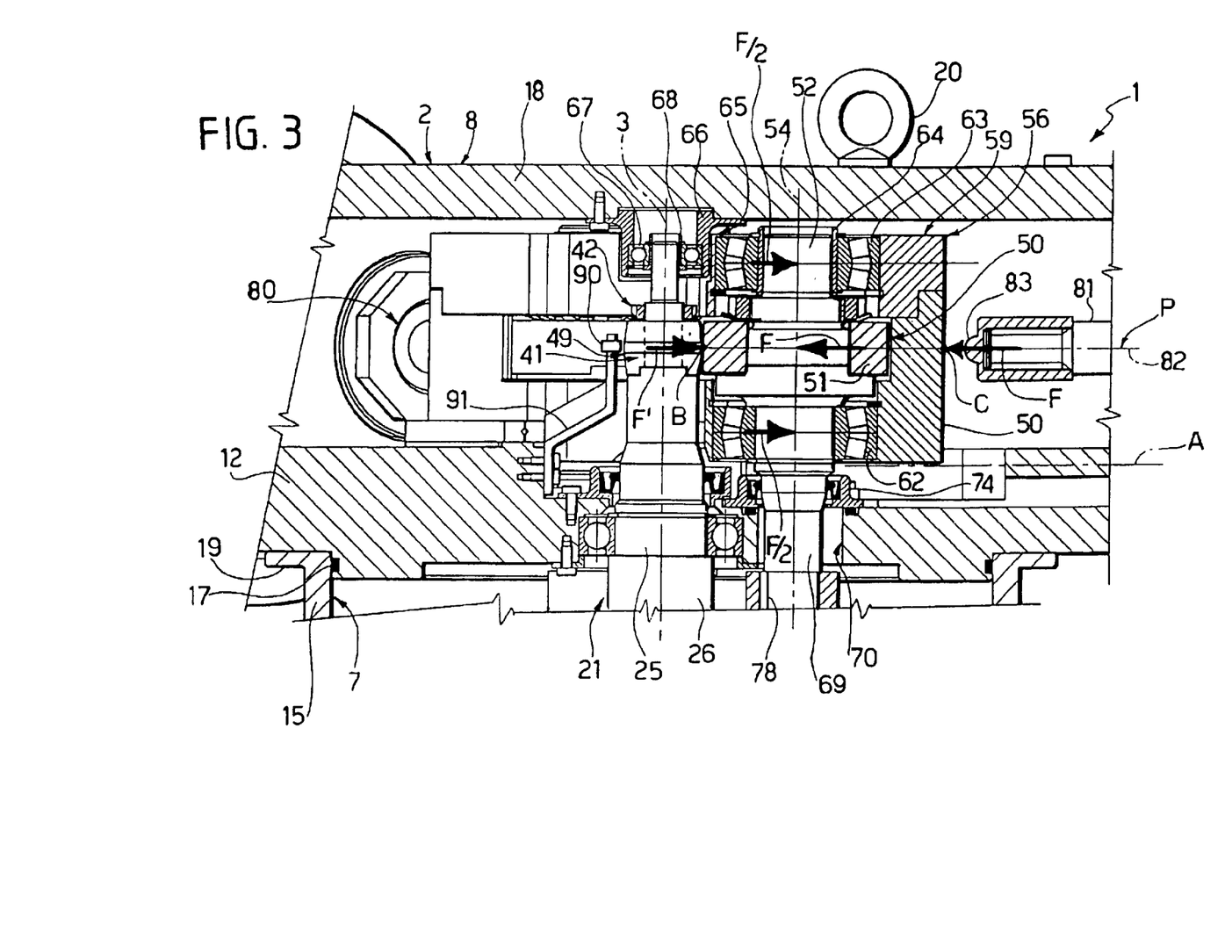
FIG. 3 is similar to FIG. 1, and shows a larger-scale view, with parts removed for clarity, of the FIG. 2 module.

As shown in FIGS. 2 to 4, shafts 52 extend along respective axes 54 parallel to axis 3, and are fitted to plate 12, equally spaced angularly about axis 3, by respective guide and slide devices 56, which have rolling-contact bodies to reduce friction phenomena, and each of which comprises a respective straight radial guide 57 fitted integrally to plate 12, preferably by screws, and a respective slide 59 comprising two supporting bodies 60, 61.

With particular reference to FIG. 4, bodies 60, 61 of each slide 59 partly house relative specimen 51, are connected integrally and releasably to each other, preferably by screws and locating pins, and support shaft 52 by means of respective identical rolling-contact bearings 62, 63 fitted in axially symmetrical positions with respect to a plane P perpendicular to axis 54. More specifically, bearing 63 is fitted to the end of shaft 52 with the interposition of a bush 64 for enabling repeated assembly and disassembly without jeopardizing the geometry of the coupling.

Body 60 is fitted to guide 57 to enable specimen 51 to translate, in a radial direction A perpendicular to axes 3, 36, between a first position, in which surfaces 49, 50 contact each other at a region whose mid-point B lies in plane P, and a second position, in which surfaces 49, 50 are detached from each other with a maximum travel of roughly 7 millimeters.

In the event of a malfunction of apparatus 1 and/or the absence or deterioration of specimens 41, 51, the travel of slide 59 towards the center is arrested by a stop device 65, which cooperates with both bodies 60, 61 to avoid excessive bending loads on slide 59, and which comprises a first shoulder (not shown) integral with plate 12, and a second shoulder defined by a bush 66 connected integrally to plate 18 and coaxial with shaft 21. Bush 66 supports the end of shaft 21 by means of a respective rolling-contact bearing 67 fitted to the end of shaft 21 with the interposition of a bush 68.

Figure 5:
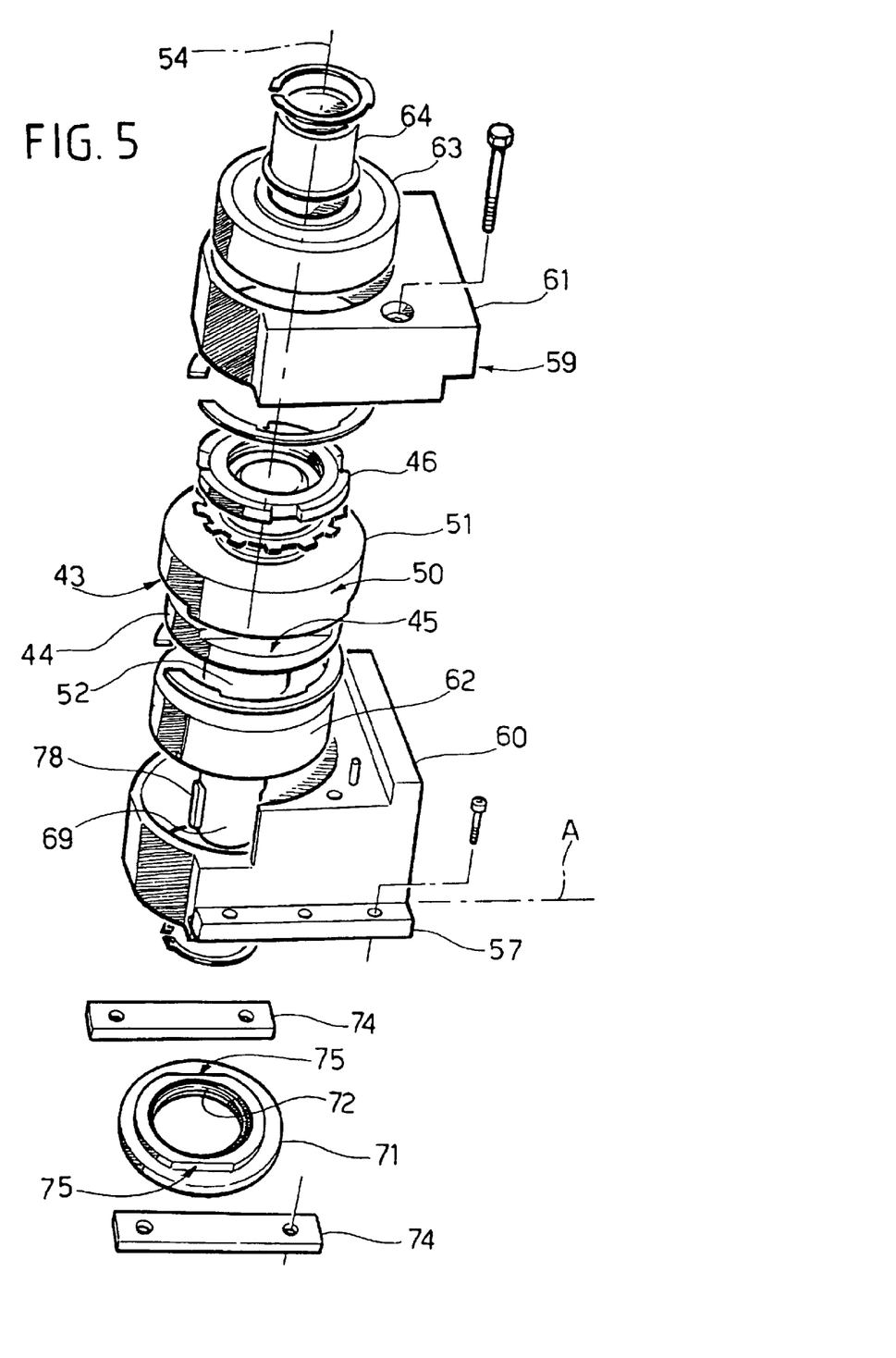
FIG. 5 shows an exploded view in perspective of part of FIG. 4.

Shafts 52 terminate beneath body 60 with respective portions 69, each of which extends loosely through a respective hole 70 through plate 12. Fluidtight sealing between each portion 69 and plate 12 is assured by a respective ring 71, which is fitted to shaft 52, is housed inside module 8, and is fitted in fluidtight manner to shaft 52 and plate 12 by the interposition of respective annular sealing members 72, 73. Ring 71 is interposed axially between plate 12 and two guide members 74, which are located diametrically opposite each other with respect to ring 71, are fixed to plate 12, preferably by screws (not shown), allow ring 71 to translate in direction A, and, at the same time, keep member (O-ring) 73 pressed axially between plate 12 and ring 71. More specifically, members 74 are fitted in sliding manner to respective flat portions 75 formed on the outer lateral surface of ring 71 to prevent ring 71 from rotating about axis 54.

As shown in FIGS. 1 and 4, shafts 52 are rotated by shafts 35, regardless of their position along guides 57, by means of respective universal transmissions 76 housed in module 7. Each transmission 76 comprises two universal joints 77, which are connected integrally to a portion 37 and a portion 69 respectively, in particular by means of key couplings 78 (not shown in detail), and are made angularly integral with each other by an intermediate splined coupling 79 (not shown in detail), which, being telescopic, allows joints 77 to part as a function of the radial position of slide 59.

With reference to FIGS. 2 and 3, apparatus 1 also comprises, for each slide 59, a respective preferably pneumatic single-acting diaphragm actuator 80 connected integrally to box 16 and for moving a rod 81 along an axis 82 lying in plane P and perpendicular to axes 3, 54. Rods 81 are housed in module 8, and terminate axially with respective portions 83, which cooperate in contact with slides 59 and are hemispherical so that the thrust or force F generated by each actuator 80 is applied at one point C. Actuators 80 are supplied in parallel by a closed-loop pneumatic feed line 85 to balance the forces F of all three actuators 80.

In actual use, each force F moves relative slide 59 in direction A along guide 57, and so presses surface 50 radially against surface 49. As shown schematically in FIG. 3, a force equal to force F and aligned with axis 82 acts at mid-point B of contact between surfaces 49, 50, by virtue of the symmetrical position of bearings 62, 63, of the particular orientation of axis 82, and therefore of the location of point C at which force F is applied.

Force F and the reaction F' of specimen 41 are therefore aligned and opposite, so that no bending stress is produced on shaft 52, specimen 51, or device 56.

During the test, besides operating actuators 80 to push slides 59 radially, specimens 41, 51 are rotated by gear train 38, so that surfaces 49, 50 roll in contact with one another and are subjected to cyclic Hertzian stress to produce rolling contact fatigue. In addition to rolling, a sliding movement between surfaces 49, 50 can also be set by appropriately selecting the diameters of specimens 41, 51 and the velocity ratio of gear train 38, i.e. the diameters of gears 39, 40, to obtain different linear surface speeds of surfaces 49, 50.

Surface 49 is thus subjected to three load cycles per turn about axis 3, and, as testing proceeds, is therefore the first to show visible macroscopic damage phenomena at subsurface level, commonly referred to as pitting.

To determine the onset of pitting phenomena, a parasitic-current proximity sensor 90 (shown schematically) is fitted to a bracket 91, facing surface 49 and detached radially from specimen 41, to determine its own distance D from surface 49 (FIG. 3), by calculating the average of values recorded over a given-sized area. More specifically, bracket 91 is fitted integrally to plate 12, preferably by screws, and is relatively rigid to prevent sensor 90 moving or vibrating during testing.

The value recorded instant by instant by sensor 90 is compared directly with a threshold value range, which, when exceeded, indicates the onset of pitting phenomena. In the presence of pitting phenomena, in fact, surface 49 tends to show marked unevenness which alters the average distance from sensor 90, so that, when sensor 90 detects an anomalous peak value, the test is stopped, and the number of load cycles undergone by specimen 41 up to that time is determined.

The mechanical components in modules 5, 6 are splash lubricated with given quantities of oil in boxes 13, 14; joints 77 in module 7 are greased; in module 8, specimens 41, 51 are oil bath lubricated, box 16 has holes (not shown) for installing heat exchangers for lubricant cooling or heating, and a thermocouple may be installed for lubricant temperature control during testing.

In a variation not shown, filler bodies are interposed between slides 59 in module 8 to reduce the amount of oil required to lubricate module 8.

Since the oil in module 8 provides solely for lubrication and can be chosen from a wide range, apparatus 1 can perform different tests of the same specimen 41, 51 material with different lubricants for comparison.

After each test, specimens 41, 51 must be changed by first taking plate 18 off box 16 and bodies 61 off slides 59, and then removing devices 46 from shafts 21, 52, and axially withdrawing specimens 41, 51 off shafts 21, 52 for replacement. Device 46 must be changed, whereas bearings 63, 67 are protected against damage during disassembly by bushes 64, 68, so need not be changed.

Specimens 51 are therefore pressed radially against specimen 41 by respective movable rods 81, as opposed to hydraulic thrust as in known solutions, so the oil in module 8 provides solely for lubrication and can be selected substantially arbitrarily. The actual in-service lubricants of the mechanical components can therefore be tested, and rolling contact fatigue tests also performed to compare different lubricants using the same specimen 41, 51 material.

Module 8 is relatively easy and cheap to assemble and disassemble, by rods 81 withdrawing axially from the slides, and by shafts 52 being guided by slides 59 to withdraw specimens 51 from specimen 41. Ensuring balanced forces F on slides 59 is also relatively easy by fitting the three actuators 80 in correct positions to box 16.

Given the space made available by movable rods 81 and slides 59, specimens 41, 51 can be replaced with others of different size and/or with differently shaped surfaces 49, 50, e.g. to obtain cylinder/cylinder, cylinder/sphere or sphere/sphere Hertzian contact.

Apparatus 1 can also be used for simply determining surface wear during rolling contact fatigue testing, given the relatively considerable maximum radial travel of specimens 51. The wear on surfaces 49, 50 during testing, in fact, is taken up by devices 56 and transmissions 76.

Moreover, shafts 52 are subjected to no bending stress during rotation, by being allowed to translate radially by devices 56 and transmissions 76, which transmit rotation regardless of the position of shafts 52. Nor are any bending moments produced on shafts 52 by forces F and reactions F', which, as stated, are aligned.

Sensor 90 is relatively easy to assemble, and supplies a measurement requiring no complex calculation, and which can be used directly to determine pitting phenomena and stop testing immediately to prevent the onset of harmful vibration.

The coupling defined by groove 43 and rib 44 eliminates the need for splined couplings, which are relatively difficult and expensive to form, on account of the relatively small inside diameter of specimen 41.

Finally, apparatus 1 being defined by independent modules 5, 6, 7, 8 makes structure 2 easy to assemble, disassemble, and maintain.

Other advantages of apparatus 1 will be clear from the foregoing description.

Clearly, changes may be made to apparatus 1 as described herein without, however, departing from the scope of the present invention.

In particular, apparatus 1 may comprise a different number of modules; slides 59 may be pushed by movable members other than rods 81; and/or motion may be transmitted from shaft 28 to shafts 21, 52 otherwise than as shown.

What is claimed is:

1. A tribological test apparatus (1) comprising:
   a supporting structure (2);
   a central shaft (21) extending along a first axis (3), connected to said supporting structure (2) to rotate about said first axis (3), and supporting a central specimen (41);
   at least three peripheral shafts (52) extending along respective second axes (54) equally spaced about said first axis (3), connected to said supporting structure (2) so as each to rotate about the respective second axis (54), and supporting respective peripheral specimens (51) radially facing said central specimen (41);
   push means (80) for exerting on each said peripheral specimen (51) a force (F) directed towards said central specimen (41); and
   relatively mobile means (56) associated with said peripheral shafts (52) to enable each said peripheral specimen (51), in use, to move radially towards said central specimen (41) and exert a contact pressure on said central specimen (41) under the action of said force (F);
   characterized in that said push means (80) comprise, for each said peripheral specimen (51), a movable push member (81) for exerting said force (F) along a push axis (82) intersecting said first (3) and said second (54) axis.

2. An apparatus as claimed in claim 1, characterized in that said relatively mobile means (56) preferably comprise, for each said peripheral shaft (52), guide and slide means (56) enabling said peripheral specimen (51) to translate between a radial contact position radially contacting said central specimen (41), and a radially detached position radially detached from said central specimen (41); transmission means (76) being provided for rotating each said peripheral shaft (52) independently of its translation.

3. An apparatus as claimed in claim 2, characterized in that said guide and slide means (56) comprise a straight guide (57) fitted to said supporting structure (2) to allow said peripheral specimen (51) to translate in a radial direction (A) with respect to said first axis (3).

4. An apparatus as claimed in claim 3, characterized in that said guide and slide means (56) comprise a slide (59) fitted in sliding manner to said guide (57) to slide in said radial direction (A), and in rotary manner to said peripheral shaft (52); said force (F) being applied by said push members (81) to said slides (59).

5. An apparatus as claimed in claim 4, characterized in that said slide (59) comprises a first and a second body (60, 61) connected integrally and releasably to each other.

6. An apparatus as claimed in claim 5, characterized in that said slide (59) is fitted to said peripheral shaft (52) by means of two bearings (62)(63) mounted axially symmetrical with respect to a plane of symmetry (P) perpendicular to said second axis (54); the application point (C) of said force (F) to each said slide (59), and the mid-point (B) of the contact region between said peripheral specimens (51) and the central specimen (41), lying in said plane of symmetry (P).

7. An apparatus as claimed in claim 6, characterized in that said push axis (82) lies in said plane of symmetry (P).

8. An apparatus as claimed in claim 4, characterized by comprising stop means (65) fitted to said supporting structure (2) to define a stop for said slide (59) towards said first axis (3).

9. An apparatus as claimed in claim 3, characterized in that said supporting structure (2) comprises a plate (12) for supporting said guides (57) and defining a number of holes (70), through each of which a respective said peripheral shaft (52) extends loosely; fluidtight sealing means (71, 72, 73) being provided between each said peripheral shaft (52) and said plate (12) to fluidtight seal the relative said hole (70).

10. An apparatus as claimed in claim 9, characterized in that said fluidtight sealing means (71, 72, 73) comprise an annular member (71) fitted in fluidtight manner to said peripheral shaft (52) and resting axially and in fluidtight manner on said plate (12).

11. An apparatus as claimed in claim 10, characterized by comprising axial-retention and guide means (74, 75) enabling radial slide of said annular member (71) on said plate (12).

12. An apparatus as claimed in claim 2, characterized in that said guide and slide means (56) have rolling-contact bodies.

13. An apparatus as claimed in claim 2, characterized in that said transmission means (76) comprise, for each said peripheral shaft (52), a relative double universal joint (77) angularly integral with the peripheral shaft (52).

14. An apparatus as claimed in claim 13, characterized in that said transmission means (76) also comprise, for each said peripheral shaft (52), a relative splined coupling (79) angularly integral with said double universal joint (77).

15. An apparatus as claimed in claim 1, characterized in that said push means (80) comprise, for each said peripheral shaft (52), a relative pneumatic actuator (80) for moving a relative said push member (81).

16. An apparatus as claimed in claim 15, characterized by comprising a pneumatic line (85) for supplying said pneumatic actuators (80); said pneumatic line (85) being a closed loop.

17. An apparatus as claimed in claim 1, characterized by comprising sensor means (90) connected integrally to said supporting structure (2) and for directly determining a characteristic (D) associated with the lateral rolling surface (49) of at least one (41) of said central and peripheral specimens.

18. An apparatus as claimed in claim 17, characterized in that said sensor means (90) comprise a proximity sensor (90) for determining its own distance (D) from said lateral rolling surface (49).

19. An apparatus as claimed in claim 18, characterized in that said sensor (90) is an induced-parasitic-current sensor.

20. An apparatus as claimed in claim 1, characterized in that said supporting structure (2) comprises a number of modules (5, 6, 7, 8) connected integrally and releasably and aligned axially with one another, and houses a number of parallel transmission shafts (21)(54, 76, 35) for rotating said central specimen (41) and said peripheral specimens (51); each said transmission shaft (21)(54, 76, 35) being divided into a number of axial portions (22, 23, 24, 25)(54, 76, 35) connected releasably to one another in angularly fixed positions and carried by different modules.

21. An apparatus as claimed in claim 20, characterized by comprising fluidtight sealing means (17) for separating said modules (5, 6, 7, 8) in fluidtight manner.

22. An apparatus as claimed in claim 20, characterized in that said supporting structure (2) comprises a first module (8) housing said central specimen (41) and said peripheral specimens (51), and supporting said push means (80) and said relatively mobile means (56).

23. An apparatus as claimed in claim 22, characterized in that said supporting structure (2) comprises a second module (6) housing a first gear train (38) for transmitting rotation from said central shaft (21) to said peripheral shafts (52).

24. An apparatus as claimed in claim 23, characterized in that said supporting structure (2) comprises a third module (7) housing a number of universal transmissions (76), each angularly integral with a relative said peripheral shaft (52).

25. An apparatus as claimed in claim 24, characterized in that said supporting structure (2) comprises a fourth module (5) housing a second gear train (32) for transmitting rotation from an input shaft (28) to said central shaft (21).

26. An apparatus as claimed in claim 1, characterized by comprising axial-positioning and angular-retention means (43, 44) for releasably fitting each said central/peripheral specimen (41, 51) to the relative said central/peripheral shaft (21, 52).

27. An apparatus as claimed in claim 26, characterized in that said axial-positioning and angular-retention means (43, 44) comprise a transverse groove (43) and a transverse rib (44) mutually engaging in axially-sliding, angularly-fixed manner.

* * * * *